United States Patent [19]

Toldy et al.

[11] 4,180,505

[45] Dec. 25, 1979

[54] NOVEL STEROIDSPIROOXAZOLIDINES AND PROCESS FOR THEIR PREPARATION

[75] Inventors: Sándor S. L. Toldy; Katalin Szilágyi née Faragó; Inge Schäfer; Eleonóra Szondy; János Borvendég; Ilona Hermann née Szente, all of Budapest, Hungary

[73] Assignee: Richter Gedeon Vegyeszet, Gyar RT, Budapest, Hungary

[21] Appl. No.: 886,349

[22] Filed: Mar. 14, 1978

[30] Foreign Application Priority Data

Mar. 14, 1977 [HU] Hungary .................................. 60 1364

[51] Int. Cl.² .............................................. C07J 21/00
[52] U.S. Cl. .............................. 260/239.55 R; 424/241
[58] Field of Search ..................................... 260/239.55

[56] References Cited

U.S. PATENT DOCUMENTS

| | | | |
|---|---|---|---|
| 3,272,801 | 9/1966 | Marshall et al. | 260/239.55 |
| 3,755,303 | 8/1973 | Nathansohn | 260/239.55 |
| 3,988,322 | 10/1976 | Kekesy et al. | 260/239.57 |
| 4,018,774 | 4/1977 | Varma et al. | 260/239.55 |

OTHER PUBLICATIONS

Leftwick, *Tetrahedron* 26, pp. 321-329 (1970).
G. W. Moersch, *J. Heterocyclic Chem.* 2,207 (1965).
E. Farkas and J. A. Swallow, *J. Med. Chem.* (1974), No. 7, p. 739.

*Primary Examiner*—Elbert L. Roberts
*Attorney, Agent, or Firm*—Karl F. Ross

[57] ABSTRACT

The invention relates to novel spirooxazolidines represented by the formula I

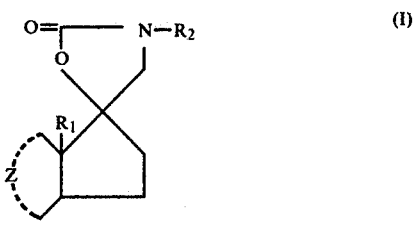

wherein
  $R_1$ is alkyl having from 1 to 4 carbon atoms;
  $R_2$ is hydrogen, alkyl having from 1 to 4 carbon atoms, alkenyl having from 1 to 4 carbon atoms, or dialkylphosphinoxymethyl having in the alkyl moiety from 1 to 3 carbon atoms each;
  z is one of the groups represented by the formulae III to XIV as subsequently defined therein.

10 Claims, No Drawings

NOVEL STEROIDSPIROOXAZOLIDINES AND PROCESS FOR THEIR PREPARATION

This invention relates to novel spirooxazolidines. More specifically, the invention relates to compounds which can be represented by the formula I

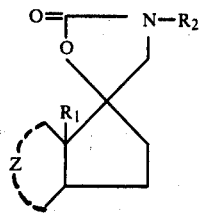
(I)

wherein $R_1$ is alkyl having from 1 to 4 carbon atoms;

$R_2$ is hydrogen, alkyl having from 1 to 4 carbon atoms, alkenyl having from 1 to 4 carbon atoms or dialkylphosphinoxymethyl having in the alkyl moiety from 1 to 3 carbon atoms each;

Z is one of the groups represented by the formulae III to XIV

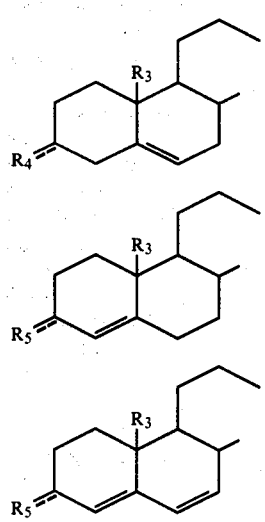

(III)

(IV)

(V)

(VI)

(VII)

(VIII)

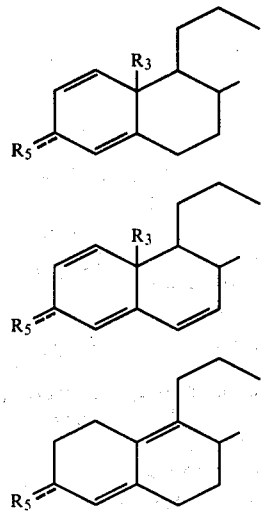

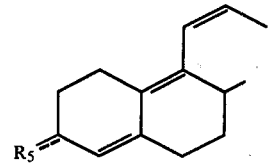
(IX)

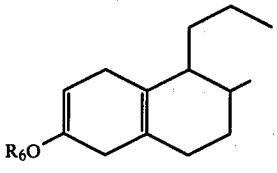
(X)

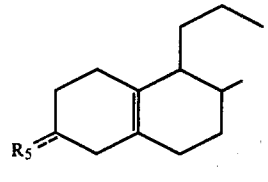
(XI)

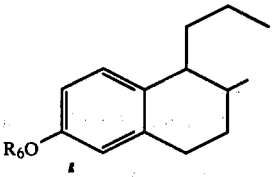
(XII)

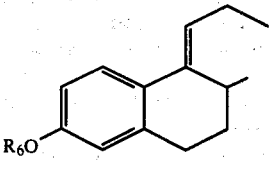
(XIII)

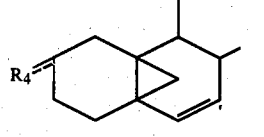
(XIV)

wherein $R_3$ is hydrogen or methyl;

$R_4$ is fluorine, hydroxyl, acyloxy having from 1 to 3 carbon atoms, alkoxycarbonyloxy having from 1 to 4 carbon atoms, oxo, oximino or alkoximino having from 1 to 3 carbon atoms;

$R_5$ is oxo, oximino or alkoximino having from 1 to 3 carbon atoms; and $R_6$ is alkyl having from 1 to 3 carbon atoms, with the proviso that if $R_1$ is methyl and Z represents a group of the formula XII, wherein $R_6$ is methyl, then $R_2$ is different from hydrogen or alkyl having from 1 to 4 carbon atoms. This invention also includes the stereoisomers of the above compounds.

A process for the preparation of the above compounds of the formula I, wherein $R_1$, $R_2$ and Z are as defined above, is also within the scope of the invention.

The new chemical compounds with which this invention is concerned can be prepared by subjecting a compound of the formula II

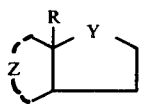

(II)

wherein
R₁ and Z are as defined above and
Y represents a group having the formula XV

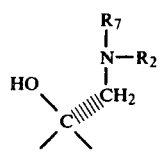

(XV)

or XVI

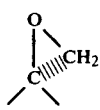

(XVI)

wherein
R₂ is as defined above and
R₇ is hydrogen or alkoxycarbonyl having from 1 to 4 carbon atoms
to ring closure, in the case of an alkoxycarbonyl R₇ alone or together with a ketone; and in other cases, by reacting with a carbonic acid derivative suitable to form an oxazolidinone group, in the presence of a base, preferably of an alkali metal hydroxide or metal alcoholate, and, if desired, the transforming the compound of the formula I thus obtained into another compound of the formula I.

The compound of the formula I so obtained is so desired may be transformed into another compound of the formula I by oxidation, halogenation and subsequent dehydrohalogenation, dehydrogenation, hydrolysis, alkylation or by transforming the 3-oxo-group or its enol ether into an oximino or alkoximino group.

The compounds of this invention possess valuable pharmaceutical properties. They show remarkable antialdosterone activity.

A valuable group of the new steroid derivatives of formula I can be prepared by subjecting to ring closure, in the presence of a base, preferably of an alkali metal hydroxide or alcoholate, a compound of the formula II—wherein
R₁ and Z are as defined above and
Y represents a group of the formula XV, wherein, R₂ is as defined above and R₇ is hydrogen or alkoxycarbonyl having from 1 to 4 carbon atoms
alone or—if R₇ stands for hydrogen—together with a carbonic acid derivative suitable to form a —C=O group.

According to a preferred embodiment of this process variant, a lower dialkyl carbonates, chlorocarbonic acid alkylester or phosgene is used as the carbonic acid derivative suitable to form a —C=O group.

Another group having advantageous pharmacological properties can be prepared by reacting a compound of formula II—wherein R₁ and Z are as defined above and Y represents a group of the formula XVI—with a carbonic acid derivative suitable to form an

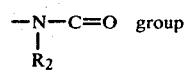 group wherein R₂ is as stated above—in the presence of a base, preferably of an alkali metal hydroxide or an alcoholate.

As the carbonic acid derivative suitable to form an

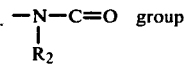 group wherein R₂ is hydrogen, alkyl or alkenyl having from 1 to 4 carbon atoms each—preferably an N-monosubstituted-carbamate or urethane or an alkyl or alkenyl isocyanate or optionally substituted urea is employed.

Further preferable compounds of formula I, in which
R₁ and R₂ are as defined above and
Z represents a group of formula IV or XIV, wherein R₃ is methyl and R₄ and R₅ each are an oxo group
—can be prepared by oxidizing a compound of formula II—wherein
Y represents a group of formula XV, wherein R₂ is as defined above and R₇ is an alkoxycarbonyl having from 1 to 4 carbon atoms;
R₁ is as defined above and
Z represents a group of formula III or XIV, wherein R₃ is methyl and R₄ is hydroxyl
with a ketone, in the presence of an aluminium alcoholate.

According to another process variant N-carbalkoxy-17α-alkylaminomethylandrost-5-en-3β-ol and the 5β,19-cycloandrost-6-en-3-ol derivatives having an analogous structure can be transformed into the corresponding steroid spirooxazolidines having the Δ⁴-3-keto-structure or bearing a 3-keto group on a cycloandrostane skeleton, in a single reaction step, since the oxidation—preferably an Oppenauer oxidation — and the ring closure take place simultaneously.

Another interesting group of compounds of formula I—in which
R₁ and R₂ are as defined above and
Z is a group having the general formula IV or XIV, wherein R₃ is methyl; R₅ is an oxo group and R₄ is an oxo group
can be prepared by oxidizing a starting compound of formula I—wherein
R₁ and R₂ as as defined above and
Z is a group of formula III or XIV, wherein R₃ is methyl and R₄ is hydroxyl
with a ketone, in the presence of an aluminium alcoholate.

By following this reaction, androst-4-en-3-on-17-spirooxazolidines are prepared by Oppenauer oxidation of the corresponding Δ⁵-3β-ol-spiroandrostone derivatives. Similarly, by the oxidation of 3-hydroxy-5β,19-cycloandrost-6-en-17-spirooxazolidines, the corresponding keto derivatives are obtained.

A further valuable group of the compounds of formula I—wherein R₁ and R₂ are as defined above and Z represents a group having formula XIV, wherein R₄ is an oxo group—can be prepared by oxidizing a starting compound of general formula I—wherein
R₁ and R₂ are as defined above and
Z stands for a group having formula XIV, wherein R₄ is hydroxyl with chromic acid.

This reaction is another variant for the transformation of 3-hydroxy-5β,19-cycloandrost-6-en-17-spirooxazolidines into the corresponding 3-keto of derivatives, in which the oxidation is performed with chromic acid.

An other advantageous group of the compounds of general formula I—wherein $R_1$ and $R_2$ are as defined above and
  Z represents a group having formula V, wherein $R_3$ is methyl and $R_5$ is an oxo group
    can be prepared by saturating a starting compound of formula I—wherein $R_1$ and $R_2$ are as defined above and
  Z represents a group having the formula III, wherein $R_3$ is as defined above and $R_4$ is hydroxy
with an equimolar amount of bromine, subsequently oxidizing the 3-hydroxy group to a ketone and eliminating 2 moles of hydrogen bromide.

In this reaction androst-5-en-3-ol-17-spirooxazolidines can be transformed into androst-4,6-dien-3-on-spirooxazolidines. This reaction can easily be accomplished by the addition of one mole of bromine to the double bond in the 5-position, subsequent oxidation of the 3-hydroxyl group with sodium bichromate in glacial acetic acid, and elimination of 2 moles of hydrogen bromide from the dibromoketone obtained in the presence of lithium bromide and lithium carbonate in dimethylformamide.

Valuable compounds of formula I — wherein $R_1$ and $R_2$ are as defined above and
  Z is a group having formula V, VI or VII, wherein $R_3$ is as defined above and $R_5$ stands for an oxo group
    can be prepared by reacting a starting compound of formula I
wherein $R_1$ and $R_2$ are as defined above and
  Z is a group having formula III, IV or V, wherein $R_3$ and $R_4$ are as defined above and $R_5$ stands for an oxo group
with a dehydrogenating agent. In this process, in addition t the $\Delta^4$, $\Delta^5$ and $\Delta^{4,6}$ double bonds, a further double bond is formed in the molecule by using a dehydrogenating agent, preferably a benzoquinone derivative. The reaction is preferably effected in dixoane with boiling. Thus for instance oxidation of spirooxazolidines having the $\Delta^4$-3-keto structure with chloranil (tetrachloro-p-benzoquinone) affords $\Delta^{4,6}$-3-keto-spiro derivatives, while $\Delta^{1,4}$-3-keto or $\Delta^{1,4,6}$-3-keto-spiro compounds are obtained if 2,3-dichloro-5,6-dicyan-p-benzoquinone (DDQ) is employed as an oxidizing agent. Starting from androst-5-en-3β-ol-17-spirooxazolidine derivatives and employing DDQ as oxidizing agent, $\Delta^{1,4,6}$-3-keto compounds are prepared.

Further advantageous compounds of formula I—wherein
  $R_1$ and $R_2$ are as defined above and
  Z represents a group having formula XI or IV, wherein $R_5$ is an oxo group and $R_3$ is hydrogen
can be obtained by hydrolyzing a starting compound of formula I—wherein
  $R_1$ and $R_2$ are as defined above and
  Z represents for a group having formula X, wherein $R_6$ is as defined above—
with an acid. In this process the acid hydrolysis of 3-alkoxy-2,5(10)-diene-steroid-17-spirooxazodines can be carried out with a weak acid, e.g. malonic acid or acetic acid, in an aqueous alcoholic solution whereby spiro compounds having the $\Delta^{5(10)}$-3-keto structure are obtained. Hydrolysis with mineral acids, e.g. with hydrochloric acid affords spiro compounds having $\Delta^4$-3-keto structure.

A further group of advantageous compounds of the formula I—wherein
  $R_1$ and $R_2$ are as defined above and
  Z represents a group having the formula XII, wherein $R_6$ is as defined above
can be prepared by reacting a starting compound of formula I—wherein
  $R_1$ and $R_2$ are as defined above and
  Z represents a group having the formula X, wherein $R_6$ is as defined above—
with bromine, in the presence of pyridine. This method makes it possible to introduce a further double bond into 19-nor-steroid-spiro oxazolidones.

A further group of valuable compounds of formula I—wherein
  $R_1$ and $R_2$ are as defined above and
  Z stands for a group having the formula VIII— wherein $R_5$ is an oxo group
can be obtained by reacting a starting compound of the formula I—wherein
  $R_1$ and $R_2$ are as defined above and
  Z represents a group having the formula XI— wherein $R_5$ is an oxo group
with bromine, in the presence of pyridine. Also this process provides a suitable means for the formation of further double bonds in 19-nor-steroid-spirooxazolidines. When reacting spiro compounds of the 3-alkoxy-2,5(10)-diene type with bromine in pyridine, 3-alkoxy-1,3,5(10)-triene-17-spirooxazolidines are obtained. Similarly, starting from $\Delta^{5(10)}$-3-keto-steroid-spirooxazolidines $\Delta^{4,9(10)}$-3-keto-spiro compounds can be prepared. These reactions can be carried out more advantageously when in place of bromine, pyridinium bromide perbromide is added into the solution of the steroid starting compound in pyridine.

Further valuable compounds of formula I—wherein
  $R_1$ and $R_2$ are as defined above and
  Z stands for a group having the formula IX—wherein $R_5$ is an oxo group
can be prepared by reacting a starting compound of formula I—wherein
  $R_1$ and $R_2$ are as defined above and
  Z represents a group having the formula VIII— wherein $R_5$ is an oxo group
with a secondary amine, hydrolyzing the obtained 3-disubstituted-amino-$\Delta^{3,5(10),9(11)}$-steroid with a weak acid, and thereafter reacting the 3-keto-$\Delta^{5(10),9(11)}$-steroid formed with a dehydrogenating agent. By the aid of this process variant, $\Delta^{4,9(10)}$-3-keto-17-spirooxazolidinyl steroids can be transformed into the corresponding enamines, preferably with pyrrolidine in methanol, and then the pyrrolidino compounds obtained are subjected to a mild acid hydrolysis, preferably with an aqueous acetic acid solution, whereby spiro compounds having the 3-keto-$\Delta^{5(10),9(11)}$ structure are obtained. When these compounds are dehydrogenated, preferably with dichlorodicyane-p-benzoquinone in dioxane, compounds having the 3-keto-$\Delta^{4,9(10),11}$ structure are prepared.

Another valuable group of the compounds having formula I—wherein
  $R_1$ and $R_2$ are as defined above and
  Z represents a group having the formula V, wherein $R_3$ is as defined above and $R_5$ stands for an oxo group can be obtained by reacting a starting compound of formula I—wherein R$_1$ and R$_2$ are as defined above and Z stands for a group having the formula IV, wherein R$_3$ is as defined above and R$_5$ stands for an oxo group with an orthoformic acid ester and then reacting the enol ether obtained with a dehydrogenating agent. This process is an advantageous way for preparing Δ$^{4,6}$-3-keto-type steroid-spiro-oxazolidines, and can be successfully used for the preparation of 19-nor-spirooxazolidines and other spirooxazolidine compounds having an androstane structure as well. The reaction of a spirooxazolidine of the Δ$^4$-3-keto structure with orthoformic acid ethylester can be carried out in the presence of an acid catalyst, preferably p-toluenesulfonic acid or a diluted solution of sulfuric acid in dioxane to obtain the corresponding enol ether which is then isolated and subsequently dehydrogenated in an aqueous acetone solution, preferably with chloranil.

A further preferred group of the compounds of formula I can be prepared by transforming a compound of formula I—wherein R$_1$ is as defined above, R$_2$ is hydrogen and Z represents one of the groups having formulae III to XIV, wherein R$_3$, R$_4$, R$_5$ and R$_6$ are as defined above into a corresponding N-alkali metal salt which is then reacted with an alkyl or alkenyl halide having from 1 to 4 carbon atoms each, or with a dialkylphosphinomethyl halide having from 1 to 3 carbon atoms or with a reactive ester, preferably a methanesulfonic acid ester of a dialkylsphosphinoxymethanol. This process is a suitable method for the preparation of N-substituted steroid 17-spirooxazolidines. According to a preferred embodiment of this reaction steroid 17-spirooxazolidines having no substituent on the nitrogen atom are reacted with sodium hydride in a suitable solvent, and the N-sodium salt obtained is alkylated in situ with an alkyl or alkenyl halide, dialkylphosphinoxymethyl halide or with a reactive ester, e.g. the methanesulfonic acid ester, of dialkylphosphinoxy-methanol.

Further preferred compounds having formula I—wherein

R$_1$ and R$_2$ are as defined above and

Z represents one of the groups represented by the formulae IV, V, VI, VII, VIII, IX or XI, wherein R$_3$ is as defined above and R$_5$ stands for an oximino or an alkoximino group having from 1 to 4 carbon atoms, or Z may stand for a group having the formula XIV, wherein R$_4$ is an oximino or an alkoximino group having from 1 to 3 carbon atoms can be prepared by reacting a starting compound of formula I—wherein R$_1$ and R$_2$ are as defined above and Z represents one of the groups of formulae IV, V, VI, VII, VIII, IX or XI, wherein R$_3$ is as defined above and R$_5$ is an oxo group, or Z represents a group having the formula XIV, wherein R$_4$ is an oxo group with hydroxylamine or with an O-alkyl-hydroxylamine having from 1 to 3 carbon atoms. In this process the starting oxo-compound is preferably reacted with hydroxylamine chlorohydrate or the O-alkyl-hydroxylamine chlorohydrate, in an aqueous alcoholic medium, in the presence of sodium acetate.

Another further preferred group of the compounds of the formula I—wherein

R$_1$ and R$_2$ are as defined above and

Z is a group having the formula IV, wherein R$_3$ is hydrogen and R$_5$ is an oximino or alkoximino group having from 1 to 3 carbon atoms can be obtained by reacting a starting compound of formula I—wherein R$_1$ and R$_2$ are as defined above and Z is a group having the formula X—wherein R$_6$ is as defined above with a hydroxylamine salt or an O-alkyl-hydroxylamine salt, in the presence of a base. This reaction provides an advantageous way for the preparation of the oximes and O-alkyl-oximes of Δ$^4$-3-keto-steroid-spirooxazolidines. According to a preferred embodiment of this process a 3-alkoxy-2,5(10)-diene-steroid-17-spirooxazolidine is reacted with hydroxylamine-chlorohydrate or an O-alkylhydroxylamine-chlorohydrate in pyridine to prepare the oxime or the corresponding O-alkyl-oxime of the Δ$^4$-3-keto-steroid-spirooxazolidinone starting compound in a single reaction step.

The preparation of certain compounds within the scope of this invention has been described in the U.S. Pat. No. 3,272,801. According to this known process a compound having formula II—wherein R$_1$ is methyl, Y is a group represented by the formula XV, wherein R$_2$ and R$_7$ are hydrogen, and Z represents a group having the formula XII, wherein R$_6$ is methyl—is reacted with phosgene in the presence of a base, and the obtained compound of formula I—wherein R$_2$ is hydrogen—is subsequently transformed into its sodium salt which is then further alkylated to give the desired compound.

Starting materials of the process according to the invention are prepared in a manner known per se from a suitable 17-keto-steroid. This compound is transformed into a corresponding steroid spirooxirane, for example, by means of dimethylsulfonium methylide ([M. Hübner and J. Noack: J. f. parkt. Chem. 314, 667 (1972)]. This reaction proceeds stereospecifically and yields spirooxiranes in which the asymmetric carbon atom in the 17-position is exclusively in the S configuration. It is also known that when using a different kind of sulfur-ylide, for instance dimethylsulfoxonium methylide, spirooxiranes having the R configuration in the 17-position can also be prepared. From enantiomeric 17-keto-steroids the corresponding enantiomeric spirooxiranes are obtained. It will be noted that the denomination of the configuration of the 17-carbon atom and of the instant compounds is in agreement with the rules layed down by the IUPAC and published in Hoppe Seylers Z. Physiol. Chem. 351, 687 (1970).

Some of the steroid-17-spirooxiranes used in the process according to the invention are novel compounds, typical representatives of which are listed hereinbelow: 13β-ethyl-3-methoxygona-2,5(10)-diene-17S-spirooxirane; ent.13β-ethyl-3-methoxygona-2,5(10)-diene-17S-spirooxirane; 3β-fluoroandrost-5-ene-17β-spirooxirane; 3-methoxyoestra-1,3,5(10),9(11)-oestratetraene-17S-spirooxirane and 3β-hydroxy-5β,19-cycloandrost-6-ene-17S-spiroxirane.

The process for the preparation of the starting compounds, the 17α-monosubstituted-aminomethyl-steroids and the N-carbalkoxy derivatives thereof, preferably involves the reaction of the corresponding steroid-17-spirooxirane with excess of the corresponding amine, in the presence of p-toluenesulfonic acid as a catalyst, with or without any solvent. The N-carbalkoxy derivatives are advantageously prepared from these compounds by reacting them with a pyrocarbonic acid dialkylester or with a chlorocarbonic acid ester, in the presence of an acid-binder agent.

The aldosterone antagonist effect of the compounds according to the invention—which means in other words that these compounds block the effect of aldosterone on the electrolyte proportion in kidney—has been tested by the method of C. M. Kagawa [C. M. Kagawa et al., J. Pharmacol. Exp. Ther. 126, 123 (1959)].

18 hours after the removal of their suprarenal glands, desoxycorticosterone acetate (DOCA) was administered to groups of rats which were simultaneously treated with the test and, respectively, the reference compounds. The reference compound, i.e. Spironolactone (17α-carboxyethyl-17β-hydroxy-7α-acetylthioandrost-4-en-3-one-lactone), was administered orally in a dose of 480 μg./animal. The $Na^+$ and $K^+$ concentrations in the urine of the treated animals were determined by flame photometry. Evaluation was made on the basis of the $Na^+/K^+$ proportions.

It was found that the mineralocorticoid effect of the DOCA was significantly inhibited by numerous compounds according to the invention.

From the data set forth in Table I it appears that the effect exerted by the test compounds is function of the dose applied. The DOCA blocking activity of the test compounds varies between 24% and 123%.

The daily dose of the novel compounds of formula I for exerting aldosterone antagonist effect amounts to 100 to 300 mg. for human adults.

The antiandrogenic activity of the compounds according to the invention—an undesirable side-effect exerted by spironolactone during protracted treating—was tested by the modified method of Dorfman (R. Dorfman: Steroids 2, 185 (1963)).

Castrated male mice weighing 25 to 30 g. each were treated with testosterone propionate (T.P.) in every second day. The total dose amounted to 300 μg./2 weeks/animal. The test compounds were administered parallel with the T. P. but daily in a subcutaneous dose of 5 mg./2 weeks/animal. The antiandrogenic activity of a given test compound was expressed in %. If the increase in weight of the vesicula seminalis gland induced by T.P. is 100%, subtracting the weight-increase induced by the combination of T.P. and the test compound from 100, the percentage inhibition is obtained.

It has been found that the inhibition caused by 5.0 and 10.0 mg./2 weeks/animal subcutaneous doses of Spironolactone was 32.5% and 50.6%, respectively. No inhibition was observed, however, when applying the test compounds in doses set forth in the attached Table II.

Certain compounds encompassed by formula I show also other hormonic activities. The antialdosterone activity exerted by 13β-ethylgona-4,9(10),11-trien-3-one-17S-spiro-5'-(2'-oxo-3'-methyloxazolidine) for instance is negligible when compared with the compounds listed in Table I, but it shows a surprisingly high antiandrogenic activity (when administered in a dose of 300 μg./2 weeks/animal, the inhibition against 300 μg./2 weeks/animal doses of T.P. amounts to 70%.

Table I

| Compound | Dose /μg/animal | Route of administration | N | log $\overline{X}$ | Na × 10 K ± | S | DOCA blocking activity | Activity related to Spironolactone |
|---|---|---|---|---|---|---|---|---|
| Oestr-4-en-3-one-17S-spiro-5'- | 480 | p.o. | 8 | 1.26 | ± | 0.49 | 61% | 1.04 |
| -(2'-oxo-3'-methyloxazolidine) | 960 | p.o. | 8 | 1.12 | ± | 0.46 | 44% | |
| Androst-4,6-dien-3-one-17S- | 480 | p.o. | 8 | 1.14 | ± | 0.29 | 46% | 0.94 |
| -spiro-5'-(2'-oxo-3'-methyl-oxazolidine) | 960 | p.o. | 8 | 1.74 | ± | 0.45 | 123% | |
| 3β-Hydroxy-5β,19-cycloandrost- | 480 | p.o. | 6 | 1.18 | ± | 0.16 | 51% | 0.98 |
| 6-ene 17S-spiro-5'-(2'-oxo-3'-methyloxazolidine) | 960 | p.o. | 6 | 1.23 | ± | 0.49 | 58% | |
| 3β-Fluoro-androst-5-ene-17S- | 480 | p.o. | 8 | 0.98 | ± | 0.20 | 26% | 0.80 |
| spiro-5'-(2'-oxo-3'-methyl-oxazolidine) | 960 | p.o. | 8 | 1.13 | ± | 0.37 | 45% | |
| 13β-Ethyl-gon-5(10)-en-3-one- | 480 | p.o. | 8 | 1.02 | ± | 0.71 | 31% | 0.84 |
| 17S-spiro-5'-(2'-oxo-3'-methyloxazolidine) | 960 | p.o. | 8 | 1.34 | ± | 0.36 | 71% | |
| 13β-Ethyl-gon-4-en-3-one- | 480 | p.o. | 28 | 1.13 | ± | 0.67 | 45% | 0.93 |
| 17S-spiro-5'-(2'-oxo-3'-methyloxazolidine) | 960 | p.o. | 40 | 1.16 | ± | 0.34 | 49% | |
|  | 1920 | p.o. | 34 | 1.30 | ± | 0.30 | 67% | |
| 13β-Ethyl-3-methoximinogon- | 480 | p.o. | 18 | 1.19 | ± | 0.13 | 53% | 0.98 |
| 4-ene-17S-spiro-5'-(2'-oxo-3'-methyloxazolidine) | 960 | p.o. | 18 | 0.97 | ± | 0.40 | 24% | |
| 13β-Ethyl-3-methoxy-gona- | 480 | p.o. | 16 | 1.16 | ± | 0.48 | 49% | 0.96 |
| 2,5(10)-diene-17S-spiro-5'-(2'-oxo-3'-(1''-cis-propenyl)-oxazolidine | 960 | p.o. | 16 | 1.22 | ± | 0.44 | 56% | |
| DOCA (Pregn-4-ene-3,20-dion-21-ol-acetate) | 12.5 | s.c. | 28 | 0.78 | ± | 0.22 | | |
| Spironolactone (17α-carboxyl-ethyl-17β-hydroxy-7αacetylthio-androst-4-en-3-one-lactone) | 480 | p.o. | 21 | 1.21 | ± | 0.22 | 54% | 1.0 |

Table II

| Compound | Dose (s.c.) mg./2 weeks/ /animal | Increase in weight of vesicula seminalis (%) | + Stimulation, % − Inhibition, % |
|---|---|---|---|
| Testosterone propionate | 0.3 | 100 | |
| Spironolactone | 5.0 | 67.5 | −32.5 |

Table II-continued

| Compound | Dose (s.c.) mg./2 weeks/ /animal | Increase in weight of vesicula seminalis (%) | + Stimulation, % − Inhibition, % |
| --- | --- | --- | --- |
|  | 10.0 | 49.4 | −50.6 |
| Androst-4,6-dien-3-one-17S-spiro-5'-(2'-oxo-3'-methyl-oxazolidine) | 5.0 | 98.6 | −1.4 |
| Oestr-4-en-3-one-17S-spiro-5'-(2'-oxo-3-methyl-oxazolidine) | 5.0 | 113.0 | +13.0 |
| 13β-Ethyl-gon-5(10)-en-3-one-17S-spiro-5'-(2'-oxo-3'-methyloxazolidine) | 5.0 | 114.0 | +14.0 |
| 13β-Ethyl-3-methoxygona-2,5(10)-diene-17S-spiro-5'-(2'-oxo-3'-/1''-cis-propenyl/-oxazolidine) | 5.0 | 112.5 | +12.5 |
| 13β-Ethyl-3-methoxymino-gon-4-ene-17S-spiro-5'(2'-oxo-3'-methyl-oxazolidine) | 5.0 | 115.0 | +15.0 |

Each group of test amimals consisted of from 8 to 10 mice.

The novel steroid derivatives with which this invention is concerned are effective diuretics having a spiro structure and may be obtained from readily available starting compounds by simple reaction steps, with an excellent yield.

Further details of this invention are to be found in the following non-limiting Examples.

EXAMPLE 1

3β-Hydroxyandrost-5-ene-17S-spiro-5'-(2'-oxo-3'-methyloxazolidine)

Step "A"

31.9 g. of androst-5-en-3β-ol-17S-spirooxirane [D. N. Kirk and M. A. Wilson: J. Chem. Soc. (C) 422 (1971)] are admixed with 3.19 g. of p-toluenesulfonic acid. 110 ml. of liquid methylamine are then added and the mixture is heated at 135° C. for 16 hours in a bomb tube. After opening the bomb tube, excess methylamine is evaporated, the residue is taken up in a small portion of water, filtered and washed to neutral. The dry raw product is dissolved in 1200 ml. of ethyl acetate while hot. The solution is evaporated to a volume of about 250 ml. and 250 ml. of n-hexane are added. Upon cooling 29.37 g. of 17α-methylaminoethylandrost-5-ene-3β,17β-diol are filtered off. M.p. 197° to 198° C.; $[\alpha]_D^{20} = -85°$ (c=0.5, chloroform).

Step "B"

To the suspension of 12.35 g. of 17α-methylaminomethylandrost-5-ene-3β,17β-diol in 130 ml. of dry dichloromethane 11.8 g. of eithyl pyrocarbonate are added portionwise, while stirring. When there is no more effervescence the solution is heated for 3 hours on a water bath and evaporated. The crysralline residue is taken up in a 1:1 mixture of cold methanol and isopropyl ether and subsequently filtered to yield 13.7 g. of crude N-ethoxycarbonyl-17α-methylaminomethylandrost-5-ene-3β,17β-diol. The obtained crude product is recrystallized from methanol. M.p. 161° C.; $[\alpha]_D^{20} = -68°$ (c=0.5, chloroform).

Step "C"

16.77 g. of N-ethoxybarbonyl-17α-methylaminomethylandrost-5-ene-3β,17η-diol are dissolved in a sodium ethylate solution prepared from 1 g. of sodium and 180 ml. of ethanol and heated for one hour at a water bath. The reaction mixture is evaporated, the residue taken up in water and filtered. 14.11 g. of crude androst-5-ene-3β-ol-17S-spiro-5'-(2'-oxo-3'-methyloxazolidine) are obtained. M.p. (after recrystallization from ethyl acetate) 213° C.; 8 $[\alpha]_D^{20} = -116°$ (c=0.5, chloroform).

This reaction step can be carried out also by using, instead of the sodium ethylate, potassium hydroxide dissolved in ethanol.

EXAMPLE 2

3β-Ethoxycarbonyloxyandrost-5-ene-17S-spiro-5'-(2'-oxo-3'-methyloxazolidine)

1.66 g. of 17α-methylaminomethylandrost-5-ene-3β,17β-diol and 16 ml. of diethyl carbonate are stirred in the presence of 0.40 g. of potassium-tert-butylate at 160° C. for 2.5 hours. The reaction mixture is evaporared to about one third of its volume and then poured onto water. 1.80 g. of the crude title compound are obtained, which are then recrystallized from 20 ml. of methanol to yield 1.43 g. of the pure title product. M.p. 190° C.; $[\alpha]_D^{20} = -92°$ (c=0.5, chloroform).

EXAMPLE 3

Androst-4-en-3-one-17S-spiro-5'-(2'-oxo-3'-methyl-oxazolidine)

Method "A"

The mixture of 9.0 g. of androst-5-en-3β-ol-17S-spiro-5'-(2'-oxo-3'-methyloxazolidine) prepared according to Example 1, 10.2 g. of aluminum isopropylate and 52 ml. of cyclohexanone is boiled in 200 ml. of dry toluene for 13 hours. Upon cooling, the reaction mixture is extracted with three portions of 50-ml. each of a 5% hydrochloric acid solution, 15 ml. of water, and 15 ml. of saturated sodium bicarbonate solution and with water. The organic phase is dried, evaporated and the oily residue triturated with isopropyl ether. The crystalline product obtained is washed with isopropyl ether on a filter. Recrystallization of the crude product from ethyl acetate affords 4.2 g. of the pure compound. M.p. 189° C.; $[\alpha]_D^{20} = +44'$(c= 0.5, chloroform). When the crude product is recrystallized from methanol, upon the addition of isopropyl ether, the melting point of the title product is different: 148° C.

Method "B"

The mixture of 2.03 g. of N-ethoxycarbonyl-17α-methylaminomethylandrost-5-en-3β-ol 5.2 ml. of c-hexamone, and 2.04 g. of aluminium isopropylate in 30 ml. of dry toluene is boiled for 7 hours. The reaction mixture is extracted with a 5% hydrochloric acid solution. Thereafter the organic phase is shaken to neutral with saturated aqueous sodium bicarbonate solution and water, dried and evaporated. From the oily residue, after triturating with isopropyl ether, 1.08 g. of crude androst-4-en-3-one-17S-spiro-5′-(2′-oxo-3′-methyloxazolidine) are obtained. M.P. (after recrystallization from ethyl acetate) 188° to 189° C.; $[\alpha]_D^{20} = +44°$ (c=0.5, chloroform).

EXAMPLE 4

3β-Hydroxyandrost-5-ene-17S-spiro-5′-(2′-oxo-3′-allyloxazolidine)

Step "A"

By following the procedure described in Example 1, Step "A" but starting from 9.06 g. of 3β-hydroxyandrost-5-ene-17S-spirooxirane and using 25 ml. of allylamine and 0.90 g. of p-toluenesulfonic acid, after recrystallization from ethyl acetate 7.72 g. of 17α-allylaminomethylandrost-5-ene-3β,17β-diol are obtained; m.p. 145° C.; $[\alpha]_D^{20} = -86°$ (c=0.5, chloroform).

Step "B"

By following the procedure described in the Example 1, Step "B" but starting from 7.18 g. of 17α-allylaminomethylandrost-5-ene-3β,17β-diol and recrystallizing the crude end-product from ethyl acetate upon addition of isopropyl ether, 6.92 g. of N-ethoxycarbonyl-17α-allylaminomethylandrost-5-end-3β,17β-diol are obtained; m.p. 148° C.; $[\alpha]_D^{20} = -57°$ (c=0.5, chloroform).

Step "C"

Ring closure of the above N-ethoxycarbonyl-N-allylaminomethyl compound carried out as described in Example 1, Step "C" affords the title compound, melting at 258° and 259° C.; $[\alpha]_D^{20} = -134°$ (c=0.5, chloroform).

EXAMPLE 5

3β-Hydroxyandrost-5-ene-17S-spiro-5′-(2′-oxo-3′-isopropyloxazolidine)

Step "A"

By following the procedure described in Example 1, Step "A" but starting from 6.04 g. of 3β-hydroxyandrost-5-ene-17S-spirooxirane and 17 ml. of isopropylamine, and using 0.60 g. of p-toluenesulfonic acid as catalyst, there are obtained 7.11 g. of 17α-isopropylaminomethylandrost-5-ene-3β,17β-diol. After recrystallization from ethyl acetate upon addition of equivalent volume of n-hexane, the product melts at 112° to 113° C.; $[\alpha]_D^{20} = -76.4°$ (c=0.5, chloroform).

Step "B"

Starting from the product of the above step "A" and proceeding as described in Example 1, Step "B", N-ethoxycarbonyl-17α-isopropylaminomethylandrost-5-ene-3β,17β-diol is obtained which, after recrystallization from ethyl acetate, melts at 144° C.; $[\alpha]_D^{20} = -74°$ (c=0.5, chloroform).

Step "C"

Ring closure of the above compound carried out as described in Example 1, Step "C" affords the title compound which, after recrystallization from ethyl acetate, melts at 222° to 223° C.; $[\alpha]_D^{20} = -117°$ (c=0.5, chloroform).

EXAMPLE 6

3β-Fluoroandrost-5-ene-17S-spiro-5′-(2′-oxo-3′-methyloxazolidine)

Step "A"

To a suspension of 8.85 g. of 3β-fluoroandrost-5-en-17-one [C. W. Shoppee and G. H. R. Summers: J. Chem. Soc. 4813 (1957)] and 14.08 g. of trimethylsulfonium iodide in 100 ml. of dry dimethyl stirred for over a quarter of an hour, 8.50 g. of potassium tert.butylate are added at 20° C. The mixture obtained is stirred for additional 2.5 hours and then poured into 1700 ml. of ice water. The precipitated crystals are filtered off and washed to neutral with water. Upon recrystallization of the crude product from methanol 7.15 g. of pure 3β-fluoroandrost-5-ene-17S-spirooxirane are obtained; m.p. 197° C.; $[\alpha]_D^{20} = -94°$ (c=0.5, chloroform).

Step "B"

By following the procedure described in Example 1, Step "A" but starting from 6.10 g. of 3β-fluoroandrost-5-ene-17S-spirooxirane and 50 ml. of liquid methylamine and using 0.60 g. of p-toluenesulfonic acid as catalyst, after recrystallization from methanol, 5.1 g. of 3β-fluoro-17α-methylaminomethylandrost-5-en-17 -ol are obtained; m.p.: 175° C.; $[\alpha]_D^{20} = -100°$ (c= 0.5, chloroform).

Step "C"

By following the procedure described in Example 1, Step "B" but starting from 3β-fluoro-17 -methylaminomethylandrost-5-en-17β-ol obtained in the above Step "B", the corresponding N-ethoxycarbonyl derivative is obtained. After recrystallization from methanol the product melts at 172° C.; $[\alpha]_D^{20} = -77°$ (c=0.5, chloroform).

Step "D"

2.10 g of 3β-fluoro-N-ethoxycarbonyl-17α-methylaminomethylandrost-5-en-17β-ol prepared as described above in Step "C" are treated according to the process set forth in Example 1, Step "C" and recrystallized from isopropyl ether to yield 1.79 g. of the title compound; m.p. 175° C.; $[\alpha]_D^{20} = -127°$ (c=0.5, chloroform).

EXAMPLE 7

Androst-4-en-3-one-17S-spiro-5′-(2′-oxo-3′-allyloxazolidine)

2.16 g. of N-ethoxycarbonyl-17α-allylaminomethylandrost-5-ene-3β,17β-diol prepared as described in Example 4, Step "B" are oxidized following the procedure set forth in Example 3, Step "B", 1.31 g. of a crude product are obtained. After recrystallization from ethyl acetate upon addition of isopropyl ether the yield amounts to 1.0 g. M.p. 131° to 132° C.; $[\alpha]_D^{20} = +7.2°$ (c=0.5, chloroform).

EXAMPLE 8

Androst-4-en-3-one-17S-spiro-5′-(2′-oxo-3′-isopropyloxazolidine)

2.1 g. of N-ethoxycarbonyl-17α-isopropylaminomethylandrost-5-ene-3β,17β-diol prepared according to Example 5, Step "B" are oxidized as described in Example 3, Step "B". The product is recrystallized from ethyl acetate upon addition of isopropyl ether to yield 0.90 g. of the title compound. M.p. 177° to 179° C.; $[\alpha]_D^{20} = +34°$ (c=0.5, chloroform).

EXAMPLE 9

Androst-4,6-dien-3-one-17S-spiro-5'-(2'-oxo-3'-methyloxazolidine)

Method "A"

The method of 3.15 g. of androst-4-en-3-one-17S-spiro-5'-(2'-oxo-3'-methyloxazolidine) prepared as described in Example 3 and 13 g. of chloranil in 44 ml. of tert-butanol is boiled for 3 hours while stirring. The reaction mixture is allowed to cool to room temperature, filtered and the filtrate evaporated. The residue is dissolved in chloroform, the insoluble substance is filtered off and the chloroform solution extracted with four 12-ml. portions of of 5% sodium hydroxide solution and two 10-ml. portions of water, and subsequently dried over magnesium sulfate. The extract is concentrated and crystallization is induced by rubbing to yield 2.75 g. of a crude dimethylformamide, After recrystallizing twice from ethyl acetate the product melts at 212° to 213° C.; $[\alpha]_D^{20} = -20.3°$ (c = 0.5, chloroform). $\lambda_{max}^{ethanol} = 282$ mμ. u.

Method "B"

To a stirred suspension of 7.18 g. of androst-5-en-3β-ol-17S-spiro-5'-(2'-oxo-3'-methyloxazolidine) prepared as described in Example 1 and 0.28 g. of powdered dry sodium acetate in 70 ml. of dry tetrahydrofurane the mixture of 3.20 g. of bromine and 10 ml. of glacial acetic acid is added dropwise, at 10° C. Some minutes after the solution of the steroid a yellow precipitate can be observed. After 0.5 hours of stirring the reaction mixture is poured onto 900 ml. of ice water, allowed to stand for a short period of time and the precipitate is filtered off with suction. The wet product is taken up in 100 ml. of glacial acetic acid and the suspension obtained is heated to 60° C. 6.56 g. of sodium bichromate. 2H₂O in 20 ml. of glacial acid are heated to 80° C. and added to the above suspension while stirring. The resulted dark solution is stirred at 60° C. for half an hour, cooled and poured onto 800 ml. of ice water. The precipitated crystalline substance is filtered with suction and washed with water. The 9.5 g. of crude dibromoketone obtained are dissolved in 100 ml. of dimethylformamide, 9.5 g. of lithium bromide and 9.5 g of lithium carbonate are added and the mixture is boiled for 1.5 hours while stirring. The crude product is poured onto ice water and separated by filtration. Yield (after recrystallization from ethyl acetate using charcoal for decoloring 4.32 g. M.p. 212° C.; $[\alpha]_D^{20} = -21°$ (c=0.5, chloroform).

EXAMPLE 10

Androst-1,4-dien-3-one-17S-spiro-5'-(2'-oxo-3'-methyloxazolidine)

2.18 g. of androst-4-en-3-one-17S-spiro-5'-(2'-oxo-3'-methyloxazolidine) prepared in Example 3 are boiled in 36 ml. of dry dioxane with 1.54 g. of 2,32,3-dichloro-5,6-dicyano-1,4-benzoquinone for 40 hours. The mixture is allowed to cool to room temperature the precipitate filtered off and the filtrate evaporated. The evaporation residue is dissolved in 70 ml. of dichloromethane and extracted with five 10 ml. portions of 1% sodium hydroxide solution and subsequently with three 10 ml. portions of water, The dichloromethane solution is dried, passed through silica gel and evaporated to yield 1.5 g. of a yellow crystalline product. After two recrystallizations from ethyl acetate, 0.62 g. of a pure product are obtained melting at 246° C.; $[\alpha]_D^{20} = 0°$ (c=0.5, chloroform); $\lambda_{max}^{ethanol} = 243$ mμ.

EXAMPLE 11

Androst-1,4,6-trien-3-one-17S-spiro-5'-(2'-oxo-3'-methyloxazolidine)

The mixture of 4.28 g. of 3β-hydroxyandrost-5-ene-17S-spiro-5'-(2'-oxo-3'-methyloxazolidine) prepared in Example 1 and 8.15 g. of 2,3-dichloro-5,6-dicyano-1,4-benzoquinone in 120 ml. of dioxane is boiled for 80 hours. The reaction mixture is treated as described in Example 10 except that the dichloromethane solution of the crude product is passed through neutral aluminia. The product is recrystallized from ethyl acetate to give 0.90 g. of the title compound, melting at 223° to 224° C.; $[\alpha]_D^{20} = -44°$ (c=0.5, chloroform); $\mu_{max}^{ethanol} = 298$ mμ, 255 mμ, 221 mμ.

EXAMPLE 12

13β-Ethyl-3-methoxygona-2,5-(10)-diene-17S-spiro-5'-(2'-oxo-3'-methyloxazolidine)

Method "A"

Step "A"

To a stirred suspension of 44.0 g. of 13β-ethyl-3-methoxygona-2,5(10)-dien-17-one and 118.8 g. of trimethylsulfonium iodide in 660 ml. of dry dimethylformamide there are added 137.2 g. of potassium-tert-butylate over half an hour at 22° C. Stirring is continued for 2 hours. The reaction mixture is then poured onto ice water and the precipitated white crystalline product is filtered off and washed with water. The crude product is dried, boiled with two-fold volume of methanol and filtered while hot. 43.1 g. of 13β-ethyl-3-methoxygona-2,5-(10)-diene-17S-spiro-oxirane melting at 183° C. are obtained. To prepare a compound of analytical grade about 1 g. of the crude product is recrystallized from 30-fold volume of ethyl acetate; m.p. 187° to 180° C.; $[\alpha]_D^{20} = +106°$ (c=0.5, chloroform).

Step "B"

Following the procedure described in Example 1, Step "A" but starting from 30 g of 13β-ethyl-3-methoxygona-2,5(10)-diene-17S-spirooxirane prepared above and 90ml. of liquid methylamine and using 3 g. of p-toluenesulfonic acid as catalyst, 26 g. of 13β-ethyl-3-methoxy-17α-methylaminomethylgona-2,5(10)-dien-17β-ol are obtained. For analytical purposes about 1 g. of the crude product is recrystallized from ethyl acetate to yield a product melting at 188° to 189° C.; $[\alpha]_D^{20} = +67°$ (c = 0.5, chloroform).

Step "C"

13.5 g. of 13β-ethyl-3-methoxy-17α-methylaminomethylgonadien-17β-ol obtained in the above Step "B" are reacted with pyrocarbonic acid diethyl ester as described in Example 1, Step "B". The obtained product is recrystallized from methanol to yield N-ethoxycarbonyl-13β-ethyl-3-methoxy- 17α-methylaminomethylgona-2,5(10)dien-17β-ol. Yield 11.0 g.; m.p. 137° C.; $[\alpha]_D^{20} = +25°$ (c 0.5, chloroform).

Step "D"

The solution of 1.04 g. of N-ethoxycarbonyl-13β-ethyl-3-methoxy-17α-methylaminomethylgona-2,5-(10)-dien-17β-ol in 15 ml. of ethanol containing 0.50 g. of potassium hydroxide is boiled for one hour. The reaction mixture is treated according to the Example 1, Step "C" and the obtained product is recrystallized from ethyl acetate to yield 0.60 g. of 13β-ethyl-3-methoxygona-2,5(10)-diene-17S-spiro-5'-(2'-oxo-3'-methyloxazolidine). M.p. 207° C.; $[\alpha]_D^{20} = +17°0$ (c=0.5, chloroform).

Method "B"

0.94 g. of 13β-ethyl-3-methoxygona-2,5-(10)-diene-17S-spirooxirane prepared according to the Example 12, Step "A" and 4.2 g. of N-methyl-urethane are stirred for three hours at 130° C., in the presence of 0.35 g. of potassium-tert-butylate. The reaction mixture is poured onto water and the precipitated crystalline substance filtered with suction and subsequently washed. The product is recrystallized from ethyl acetate. Yield: 0.60 g.; m.p. 206° to 207° C.; $[\alpha]_D^{20} = +16.7°$ (c=0.5, chloroform).

Method "C"

18.5 g. of 13β-ethyl-3-methoxy-∫α-methylaminomethylgona-2,5(10)-dien-17β-ol in 190 ml. of dry diethyl carbonate are stirred for three hours at 160° C., in the presence of 6.0 g. of potassium-tert-butylate. The reaction mixture is evaporated and the residue taken up in water. The resulted crystalline product is filtered with suction and washed with water to yield crude 13β-ethyl-3-methoxygona- 2,5(10)-diene-17S-spiro-5'-(2'-oxo-3'-methyloxazolidine). After recrystallization from ethyl acetate 15.0 g. of a pure product melting at 207° to 208° C. are obtained; $[\alpha]_D^{20} = +17.6°$ (c=0.5, chloroform). The product does not shpw any decrease in melting point when admixed with the products of Example 12, Methods "A" and "B".

EXAMPLE 13

13β-Ethyl-3-methoxygona-2,5(10)-diene-17S-spiro-5'-(2'-oxo-3'-ethyloxazolidine)

Step "A"

By following essentially the procedure described in Example 12, Method "A", Step "B" 13β-ethyl-3-methoxy-17α-ethylaminomethylgona-2,5(10)-dien-17β-ol melting at 186° C. is obtained; $[\alpha]_D^{20} = +60°$ (c=0.5, chloroform).

Step "B"

6.15 g. of 13β-ethyl-3-methoxy-17α-ethylaminomethylgona-2,5(10)-dien-17β-ol are treated as described in Example 12, Method "C" and the crude product obtained is recrystallized from ethyl acetate and subsequently from methanol to yield 4.37 g. of 13β-ethyl-3-methoxygona-2,5(10)-diene-17S-spiro-5'-(2'-oxo-3'-ethyloxazolidine); m.p. 161° C.; $[\alpha]_D^{20} = +16°$ (c=0.5, chloroform).

EXAMPLE 14

13β-Ethyl-3-methoxygona-2,5(10)-diene-17S-spiro-5'-(2'-oxo-3'-(1''-cis-propenyl)-oxazolidine)

Step "A"

By following the procedure described in Example 12, Method "A", Step "B" but using allylamine in the reaction, 13β-ethyl-3-methoxy-17α-allylaminomethylgona-2,5(10)-dien-17β-ol melting at 154° C. is obtained; $[\alpha]_D^{20} = +51°$ (c=0.5, chloroform).

Step "B"

By following the procedure described in Example 12, Method "C" but starting from 12.0 g. of 13β-ethyl-3-methoxy-17α-allylaminomethylgona-2,5(10)-dien-17β-ol in 120 ml. of diethyl carbonate and 3.63 g. of potassium-tert-butylate, 9.3 g. of 13β-ethyl-3-methoxygona-2,5(10)diene-17S-spiro-5'-[2'-oxo-3'-(1''-cis-propenyl)-oxazolidine] are obtained melting after recrystallization from ethyl acetate at 143° C.; $[60]_D^{20} = -18°$ (c=0.5, chloroform).

EXAMPLE 15

13β-Ethyl-4-en-3-one-17S-spiro-5'-(2'-oxo-3'-methyloxazolidine)

4.0 g. of 13β-ethyl-3-methoxygona-2,5(10)-diene-17S-spiro-5'-(2'-oxo-3'-methyloxazolidine) prepared as described in Example 12 are stirred in the mixture of 40 ml. of methanol, 4 ml. of water and 2 ml. of concentrated hydrochloric acid for one hour, at 60° C. The reaction mixture is evaporated, and the residue is taken up in water. The crystalline substance is suction-filtered dried and recrystallized from ethyl acetate. 2.5 g. of the pure title compound are obtained with a melting point of 192° C.; $[\alpha]_{365}^{20} = -414°$ (c=0.5, chloroform).

EXAMPLE 16

13β-Ethylgon-4-en-3-one-17S-spiro-5'-(2'-oxo-3'-ethyloxazolidine)

Starting from the compound of Example 13 and following the procedure described in Example 15 the title compound of this example is obtained. M.p. 168° C.; $[\alpha]_D^{20} = -4.9$ (c=0.5, chloroform).

EXAMPLE 17

13β-Ethylgon-5(10)-en-3-one-17S-spiro-5'-(2'-oxo-3'-methyloxazolidine)

The mixture of 4.2 g. of malonic acid, 70 ml. of water and 170 ml. of ethanol is heated to 70° C. and the suspension of 7.4 g. of 13β-ethyl-3-methoxygona-2,5(10)-diene-17S-spiro-5'-(2'-oxo-3'-methyloxazolidine) prepared as described in Example 12 in 80 ml. of ethanol is added while stirring. In several minutes a solution is obtained which is then kept at 70° C. for a further 20 minutes. 200 ml. of saturated sodium bicarbonate solution and subsequently 400 ml. of water are added dropwise to the solution under ice cooling. The precipitate formed is filtered and washed with water to yield 6.8 g. of the title compound melting at 162° to 166° C. An analytical sample of about 1 g. is dissolved in cold acetone, isopropyl ether is added and the mixture is cooled. The precipitated crystals are suction-filtered. The obtained product melts at 167° C.; $[\alpha]_D^{20} = +51°$ (c=chloroform).

EXAMPLE 18

13β-Ethylgona-4,9(10)-dien-3-one-17S -spiro-5'-(2'-oxo-3'-methyloxazolidine)

To a stirred solution of 11.1 g. of 13β-ethylgona-5(10)-en-3-one-17S-siro-5'-(2'-oxo-3'-methyloxazolidine) prepared in Example 17 in 50 ml. of dry pyridine a solution of 10.0 g. of pyridinium perbromide in 50 ml. of pyridine is added dropwise, over 40 minutes at 20° C. The reaction mixture is then stirred for 3.5 hours at room temperature and subsequently poured onto one liter of water. The oily substance crystallizes upon scratching. Recrystallization of 8.38 g. of the crude title compound from ethyl acetate yields 6.3 g. of pure compound. M.p. 165° to 167° C.; $[\alpha]_D^{20} = -265°$ (c=0.5, chloroform); $\lambda_{max}^{ethanol} = 301$ m$\mu$.

EXAMPLE 19

13$\beta$-Ethyl-3-methoxygona-1,3,5(10)-triene-17S-spiro-5'-(2'-oxo-3'-methyloxazolidine)

Starting from 1.78 g. of 13$\beta$-ethyl-3-methoxygona-2,5(10)-diene-17S-spiro-5'-(2'-oxo-3'-methyloxazolidine) prepared according to Example 12 the procedure described in Example 18 is followed. Recrystallization of the crude product from ethyl acetate yields 1.19 g. of the pure title compound melting at 197° to 198° C. $[\alpha]_D^{20} = -29°$ (c=0.5, chloroform); $\lambda_{max}^{ethanol} = 276$ m$\mu$, 284 m$\mu$.

EXAMPLE 20

13$\beta$-Ethylgona-4,9(10),11-trien-3-one-17S-spiro-5'-(2'-oxo-3'-methyloxazolidine)

To a stirred solution of 3.55 g. of 13$\beta$-ethylgona-4,9(10)-dien-3-one-17S-spiro-5'-(2'-oxo-3'-methyloxazolidine) prepared according to Example 18 in 35 ml. of dry ethanol 0.85 g. of pyrrolidine are added at room temperature under a nitrogen atmosphere. After one hour of stirring precipitation of a yellow crystalline substance can be observed. After 4 hours the suspension is cooled on an icy water bath, the yellow enamino compound is filtered with suction and subsequently washed with icy cool methanol. 2.65 g. of the enamino compound are obtained.

To a stirred suspension of the above enamino compound with 5 ml. of methanol and 2.5 ml. of water, there are added 1.20 ml. of acetic acid under a nitrogen atmosphere, at 20° C. After two hours of stirring a further 25-ml. portion of water is added and stirring is continued for further 12 hours. The reaction mixture is diluted with further 100 ml. of water, the precipitate is filtered off and washed with water. The obtained crude 13$\beta$-ethylgona-5(10),9(11)-dien-3-one-17S-spiro-5'-(2'-oxo-3'-methyloxazolidine) is dried, dissolved in acetone at room temperature, decolored with charcoal, concentrated to ¼ of its original volume and finally diluted with isopropyl ether. The precipitated 1.40 g. of 13$\beta$-ethylgona-5(10),9(11)-dien-3-one-17S-spiro-5'-(2'-oxo-3'-methyloxazolidine) melts at 174° to 176° C. To the solution of 0.49 g. of this compound in 10 ml. of dry dioxane the solution of 0.62 g. of 2,3-dichloro-5,6-dicyano-1,4-benzoquinone in 14 ml. of dioxane is added under a nitrogen atmosphere. The reaction mixture is stirred for 2 hours in the darkness, then filtered, and the dioxane filtrate is evaporated. The residue is dissolved in dichloromethane and the solution is extracted with 1% aqueous sodium hydroxide solution and subsequently with water. After drying and evaporating the extract, a yellow oily substance is obtained which recrystallizes upon trituration with isopropyl ether. 0.34 g. of crude 13$\beta$-ethylgona-4,9(10),11-trien-3-one-17S-spiro-5'-(2'-oxo-3'-methyloxazolidine) are obtained which melts after recrystallization from ethyl acetate at 225° to 226° C.; $[\alpha]_D^{20} = -88°$ (c=0.5, chloroform); $\lambda_{max}^{ethanol} = 335$ m$\mu$, 235 m$\mu$.

EXAMPLE 21

13$\beta$-Ethylgona-4,6-dien-3-one-17S-spiro-5'-(2'-oxo-3'-methyloxazolidine)

1 g. of 13$\beta$-ethylgona-4-en-3-one-17S-siro-5'-(2'-oxo-3'-methyloxazolidine) is dissolved in 20 ml. of dry dioxane, 1 ml. of orthoformic acid ethyl ester and 0.1 ml. of a solution prepared from 0.35 ml. of concentrated sulfuric acid and 7 ml. of dry dioxane are then added to the solution which is stirred for one hour at room temperature. Two drops of pyridine are added and the mixture is poured to 200 ml. of icy water. The precipitate formed is filtered off, washed with water and dissolved while wet in 7.3 ml. of acetone. 0.39 g. of chloranil are added and the solution is stirred at room temperature for 1.5 hours in darkness. It is then evaporated and the evaporation residue is dissolved in 20 ml. of dichloromethane. The dichloromethane solution is dried, passed through neutral alumina and evaporated. Upon recrystallization of the evaporation residue from ethyl acetate 0.17 g. of a pure product are obtained. M.p. 267° to 268° C.; $[\alpha]_D^{20} = -02°$ (c=0.5, chloroform; $\lambda_{max}^{ethanol} = 282$ m$\mu$.

EXAMPLE 22

13$\beta$-Ethyl-3-methoxygona-2,5(10)-diene-17S-spiro-5'-(2'-oxooxazolidine)

The mixture of 0.94 g. of 13$\beta$-ethyl-3-methoxygona-2,5(10)-diene-17S-spirooxirane obtained in Example 12, Method "A", Step "A", 3.60 g. of urethane and 0.70 g. of potassium tert-butylate in 6 ml. of hexamethylphosphoric acid triamide is stirred at 150° C. for 16 hours. The reaction mixture is poured into water and the precipitated crystalline product filtered with suction and subsequently washed with water. Recrystallization of the product from m ethanol, using charcoal for decolouring, gives 0.45 g. of the title compound. M.p 244° to 245° C.; $[\alpha]_D^{20} = +30°$ (c=0.5, chloroform).

EXAMPLE 23

13$\beta$-Ethylgon-4-en-3-one-17S-spiro-5'-(2'-oxo-oxazolidine)

4.0 g. of 13$\beta$-ethyl-3-methoxygona-2,5(10)-diene-17S-spiro-5'-(2'-oxooxazolidine) prepared as described in Example 22 are hydrolyzed according to the process set forth in Example 15. Recrystallization of the 3.45 g. of crude product from ethanol containing 35% water and subsequently from a 1:1 mixture of ethanol and ethyl acetate yields the title substance melting at 188° C. $[\alpha]_D^{20} = +15°$ (c=0.5, chloroform).

EXAMPLE 24

3-Methoxyoestra-1,3,5(10),9(11)-tetraene-17S-spiro-5'-(2'-oxo-3'-methyloxazolidine)

Step "A"

By following the procedure described in Example 12, Method "A", Step "A", but starting from 3-methoxyoestra-1,3,5(10),9(11)-tetraen-17-one, 3-methoxyoestra-1,3,5(10),9(11)-tetraene-17S-spirooxirane melting, after recrystallization from methanol, at 142° C. is obtained; $[\alpha]_D^{20} = +126°$ (c=1, chloroform).

Step "B"

By following the procedure described in Example 12, Method "A", Step "B" from 4.80 g. of the above 3-methoxyoestra-1,3,5(10),9(11)-tetraene-17S-spirooxirane 3.0 g. of 3-methoxy-17α-methylaminomethyloestra-1,3,5(10),9(11)-tetraen-17β-ol melting at 134° to 135° C. are obtained; $[\alpha]_D^{20} = +90°$ (c=0.5, chloroform).

Step "C"

By following the procedure described in Example 1, Step "B" but starting with 3.0 g. of 3-methoxy-17α-methylaminomethyloestra-1,3,5(10),9(11)-tetraen-17β-ol prepared above, the corresponding N-carbethoxy derivative is prepared. The crude product is transformed into the corresponding spiro compound in ethanol in the manner described in Example 1, Step "C". The product is recrystallized from methanol to yield 2.21 g. of the title compound melting at 187° C.; $[\alpha]_D^{20} = +10°$ (c=0.5, chloroform).

EXAMPLE 25

3-Methoxyoestra-2,5(10)-diene-17S-spiro-5'-(2'-oxo-3'-methyloxazolidine)

Step "A"

By following the procedure described in Example 12, Method "A", Step "B" but starting from 13.0 g. of 3-methoxyoestra-2,5(10)-diene-17S-spirooxirane, a crude product is obtained which is then recrystallized from methanol to yield 10.1 g. of 3-methoxy-17α-methylaminomethyloestra-2,5(10)-dien-17β-ol. M.p. 136° to 137° C.; $[\alpha]_D^{20} = +87°$ (c=0.5, chloroform).

Step "B"

12.0 g. of 3-methoxy-17α-methylaminomethyloestra-2,5(10)-dien-17β-ol in 120 ml. of dry diethyl carbonate, in the presence of 6.0 g. of potassium tert-butylate are stirred at 130° C. for 2 hours. The reaction mixture is evaporated and the residue taken up in water, filtered and washed to neutral with water. Recrystallization from ethyl acetate yields 9.35 g. of the pure title compound melting at 177° C.; $[\alpha]_D^{20} = +20.8°$ (c=0.5, chloroform).

EXAMPLE 26

Oestr.4-en-3-one-17S-spiro-5'-(2'-oxo-3'-methyloxazolidine)

8.7 g. of 3-methoxyoestra-2,5(10)-diene-17S-spiro-5'-(2'-oxo-3'-methyloxazolidine) prepared as described in Example 25 are hydrolyzed as described in Example 15. Recrystallization of the crude product from ethyl acetate results in the pure title compound which melts at 187° C. Over that temperature the crystals are rearranged and melt at 197° to 198° C. $[\alpha]_{D\ 20} = -10°$ (c=0.5, chloroform).

Example 27

Oestr-5(10)-en-3-one-17S-spiro-5'-(2'-oxo-3'-methyloxazolidine)

4.6 g. of 3-methoxyoestra-2,5(10)-diene-17S-spiro-5'-(2'-oxo-3'-methyloxazolidine) prepared as described in Example 25 are hydrolyzed as described in Example 17 whereby 3.24 g. of the title compound are obtained. An analytical sample of about 1 g. is recrystallized as set forth in Example 17 to give a pure product melting at 160° to 162° C.; $[\alpha]_D^{20} = +68°$ (c=0.5, chloroform).

EXAMPLE 28

Oestr-4,9(10)-dien-3-one-17S-spiro-5'-(2'-oxo-3'-methyloxazolidine)

2.79 g. of the product of Example 27 are treated as described in Example 18. Recrystallization of the obtained crude product from ethyl acetate yields 1.68 g. of the title compound melting at 172° to 173° C.; $[\alpha]_D^{20} = -267°$ (c=0.5, chloroform); $\lambda_{max}^{ethanol} = 301$ mμ.

EXAMPLE 29

3-Methoxyoestra-2,5(10)-diene-17S-spiro-5'-(2'-oxooxazolidine)

The mixture of 4.26 g. of 3-methoxyoestra-2,5(10)-diene-17S-spirooxirane and 17 g. of urethane in 28 ml. of hexamethylphosphoric triamide is stirred in the presence of 1.68 g. of potassium tert-butylate, under a nitrogen atmosphere, at 150° C. for 6 hours. The reaction mixture is poured into water and the separated oily substance is extracted with ethyl acetate. The ethyl acetate phase is washed with water, dried and subsequently evaporated. The crystalline residue is washed with isopropyl ether on the filter and recrystallized from methanol. 2.15 g. of the title compound melting at 231° C. are obtained; $[\alpha]_D^{20} = +30°$ (c=0.5, chloroform).

EXAMPLE 30

Oestr-4-en-3-one-17S-spiro-5'-(2'-oxooxazolidine)

1.70 g. of 3-methoxyoestra-2,5(10)-diene-17S-spiro-5'-(2'oxooxazolidine) prepared as described in Example 29 are hydrolyzed as described in Example 15. Recrystallization of the obtained crude product from ethanol yields 0.90 g. of the title compound melting at 243° to 244° C.; $[\alpha]_D^{20} = +6.9°$ (c=0.5, chloroform).

EXAMPLE 31

Oestr-4,6-dien-3-one-17-spiro-5'-(2'-oxo-3'-methyloxazolidine)

To a stirred suspension of 2.13 g. of oestr-4-en-3-one-17S-spiro-5'-(2'-oxo-3'-methyloxazolidine) prepared as described in Example 26 and 2.6 ml. of orthoformic acid ethyl ester in 17 ml. of dry ethanol are added 4 drops of the solution of 0.35 ml. of concentrated sulfuric acid in 4 ml. of dry dioxane at 5° C. Stirring is continued at 18° to 20° C. After some minutes of stirring a clear solution is obtained. After 2.5 hours of reaction, the solution is poured into 250 ml. of an icy 10% aqueous potassium carbonate solution. After a short stirring period the precipitate is filtered and washed with water. The wet substance is added into 30 ml. of acetone containing 1.53 g. of chloranil and 5% of water while stirring, and stirring is continued for further 15 hours in darkness. The reaction mixture is filtered, evaporated at room temperature, the residue dissolved in dichloromethane and the solution passed through a neutral alumina layer. Evaporation of the solution gives 1.2 g. of a yellow crude product which is then recrystallized from ethyl acetate. M.p. 228° C.; $[\alpha]_D^{20} = -85°$ (c=0.5, chloroform); $\lambda_{max}^{ethanol} = 281$ mμ.

EXAMPLE 32

3β-Hydroxy-5β,19-cycloandrost-6-ene-17S-spiro-5'-(2'-oxo-3'-methyloxazolidine)

Step "A"

To the suspension of 5.45 g. of 3β-acetoxy-5β,19-cycloandrost-6-en-17-one (O. Halpern et al.: Steroids 4, 1 (1964) and 6.8g. of trimethylsulfonium iodide in 53 ml. of dry dimethyl formamide there are added 5.6 g. of potassium tert-butylate at 10° C., in about 10 minutes.

The mixture is stirred for further 15 minutes and thereafter poured onto icy water. The precipitated substance is filtered off, washed to neutral with water and dried. Recrystallization from ethyl acetate yields 2.47 g. of 3β-hydroxy-5β,19-cycloandrost-6-ene-17S-spirooxirane melting at 180° to 181° C.; $[\alpha]_D^{20} = -15.7°$ (c=0.5, chloroform).

Step "B"

By following the procedure described in Example 1, Step "A" but starting from 2.47 g. of 3β-hydroxy-5β,19-cycloandrost-6-ene-17S-spirooxirane, 3β,17β-dihydroxy-17α-methylaminomethyl-5β,19-cycloandrost-6-ene is obtained. The crude product is recrystallized from ethyl acetate to give 1.88 g. of a pure product melting at 198° to 199° C.; $[\alpha]_D^{20} = -43°$ (c=0.5, chloroform).

Step "C"

1.80 g. of 3β,17β-dihydroxy-17α-methylaminomethyl-5β,19-cycloandrost-6-ene as prepared in Step "B" are transformed into the corresponding N-ethoxycarbonyl compound following the procedure set forth in Example 1, Step "B", and after isolation, the crude product is transformed into 3β-hydroxy-5β,19-cycloandrost-6-ene-17S-spiro-5'-(2'-oxo-3'-methyloxazolidine) as described in Example 1, Step "C". Recrystallization of the crude product from ethyl acetate yields 1.17 g. of a pure product melting at 228° to 229° C. $[\alpha]_D^{20} = -79°$ (c=1, chloroform).

EXAMPLE 33

3-Oxo-5β,19-cycloandrost-6-ene-17S-spiro-5'-(2'-oxo-3'-methyloxazolidine)

To the stirred suspension of 5.30 g. of chromium trioxide-pyridine complex (J. C. Collins et al.: Tetrahedron Lett., 3363 (1968) in 80 ml. of dry dichloromethane the solution of 0.85 g. of 3β-hydroxy-5β,19-cycloandrost-6-ene-17S-spiro-5'-(2'-oxo-3'-methyloxazolidine) prepared according to Example 32, in 18 ml. of dry dichloromethane is added dropwise at room temperature. The reaction mixture is stirred for 20 hours and subsequently filtered off. The dichloromethane solution is shaken with water, dried and passed through a neutral alumina layer. The solution is evaporated and the dry residue obtained is recrystallized from ethyl acetate to yield 0.50 g. of the pure title compound. M.p. 164° C.; $[\alpha]_D^{20} = -46.5°$ (c=0.5, chloroform).

EXAMPLE 34

3β-Hydroxyandrost-5-ene-17S-spiro-5'-(2'-oxooxazolidine)

The suspension of 3.02 g. of 3β-hydroxyandrost-5-ene-17S-spirooxirane, 4.50 g. of urethane and 0.60 g. of sodium methylate in 15 ml. of hexamethylphosphoric triamide is stirred under a nitrogen atmosphere at 140° C. for 16 hours. The reaction mixture is then poured onto 230 ml. of icy water, the precipitate is filtered off with suction and thoroughly washed with water. Recrystallization of the dry substance from methanol yields 1.25 g. of the pure title compound melting at 325° to 327° C.; $[\alpha]_D^{20} = -95°$ (c=0.5, methanol).

EXAMPLE 35

Ent. 13β-ethylgona-4-en-3-one-17S-spiro-5'-(2'-oxo-3'-methyloxazolidine)

Step "A"

By following the procedure described in Example 12, Method "A", Step "A", but starting from ent. 13β-ethyl-3-methoxygona-2,5(10)-dien-17-one, there is obtained ent. 13β-ethyl-3-methoxygona-2,5(10)-diene-17S-spirooxirane. M.p. 184° C.; $[\alpha]_D^{20} = -109°$ (c=0.5, chloroform).

Step "B"

Ent. 13β-ethyl-3-methoxygona-2,5(10)-diene-17S-spirooxirane obtained in Step "A" above is reacted with methylamine as described in Example 12, Method "A", Step "B" and the obtained product is subsequently transformed into the corresponding N-ethoxycarbonyl derivative following the procedure set forth in Example 12, Method "A", Step "C". Transformation of this compound according to Example 12, Method "A", Step "D" yields ent. 13β-ethyl-3-methoxygona-2,5(10)-diene-17S-spiro-5'-(2'-oxo-3'-methyloxazolidine) melting at 208° C. $[\alpha]_D^{20} = -19°$ (c=0.5, chloroform).

Step "C"

Ent. 13β-ethyl-3-methoxygona-2,5(10)-diene-17S-spiro-5'-(2'-oxo-3'-methyloxazolidine) is hydrolyzed with hydrochloric acid in an aqueous methanolic solution as described in Example 15 whereby ent. 13β-ethylgon-4-en-3-one-17S-spiro-5'-(2'-oxo-3'-methyloxazolidine) melting at 191° C. is obtained; $[\alpha]_{365}^{20} = +413°$ (c=0.5, chloroform).

EXAMPLE 36

13β-Ethyl-3-oximinogon-4-ene-17S-spiro-5'-(2'-oxo-3'-methyloxazolidine)

Method "A"

The solution of 0.90 g. of 13β-ethylgon-4-en-3-one-17S-spiro-5'-(2'-oxo-3'-methyloxazolidine) prepared according to Example 15, 0.20 g. of hydroxylamine chlorohydrate and 0.25 g. of dry sodium acetate in the mixture of 3 ml. of water and 20 ml. of ethanol is boiled at a water bath for one hour. The reaction mixture is evaporated, the crystalline residue washed, dried and recrystallized from methanol to yield 0.50 g. of a product melting at 284° to 286° C.; $[\alpha]_D^{20} = +86°$ (c=0.5, chloroform).

Method "B"

The solution of 1 g. of 13β-ethyl-3-methoxygona-2,5(10)-diene-17S-spiro-5'-(2'-oxo-3'-methyloxazolidine) and 1 g. of hydroxylamine chlorohydrate in 10 ml. of dry pyridine is stirred at 50° C. for 0.5 hours and at 80° C. for a further 4 hours. The reaction mixture is evaporated. The residue is dissolved in chloroform and the solution is subsequently shaken with a 2.5% aqueous hydrochloric acid solution, then with saturated sodium bicarbonate solution and finally with water. The chloroform solution is dried and evaporated. Recrystallization of the crystalline residue from methanol yields 0.50 g. of 13β-ethyl-3-oximinogon-4-ene-17S-spiro-5'-(2'-oxo-3'-methyloxazolidine) melting at 283° C.; $[\alpha]_D^{20} = +70°$ (c=0.5, chloroform).

The oximes prepared according to the above Methods "A" and "B" are mixtures of the Z and E isomers of different ratios.

EXAMPLE 37

13β-Ethyl-3-methoxyiminogon-4-ene-17S-spiro-5'-(2'-oxo-3'-methyloxazolidine)

By following the procedure described in Example 36, Method "A" but using O-methylhydroxylamine chlorohydrate and continuing the reaction for 5 hours the title compound is obtained which melts, after recrystallization from ethyl acetate, at 180° to 182° C; $[\alpha]_D^{20} = +85°$ (c=0.5, chloroform).

EXAMPLE 38

13β-Ethyl-3-allyloximinogon-4-ene-17S-spiro-5'-(2'-oxo-3'-methyloxazolidine)

By following the procedure set forth in Example 36, Method "A" but using O-allylhydroxylamine chlorohydrate the title compound is obtained; m.p. (after recrystallization from methanol) 163° to 165° C.; $[\alpha]_D^{20} = +73°$ (c=0.5, chloroform.

EXAMPLE 39

Oestr-4-en-3-one-17S-spiro-5'-(2'-oxo-3'-ethyloxazolidine)

Step "A"

1.88 g. of 3-methoxyoestra-2,5(10)-diene-17S-spiro-5'-(2'-oxooxazolidine) prepared according to Example 29 are dissolved in the mixture of 20 ml. of dry tetrahydrofurane and 40 ml. of dry benzene. 0.33 g. of sodium hydride containing 20% of paraffin are added to the solution while stirring. The temperature of the reaction mixture is kept at room temperature by the aid of a water bath. After about half an hour the gas evolution ceases; then 15 ml. of ethyl iodide are added and the mixture is boiled for 20 hours while stirring. Therafter, 5 ml. of ethanol are added to the reaction mixture, which is then evaporated to dryness. The crystalline residue is washed to neutral on the filter, dried, and recrystallized from ethyl acetate to yield 1.34 g. of 3-methoxyoestra-2,5(10)-diene-17S-spiro-5'-(2'-oxo-3'-ethyloxazolidine) melting at 178° C.; $[\alpha]_D^{20} = +18.7°$ (c=0.5, chloroform).

Step "B"

Hydrolysis of the 3-methoxyoestra-2,5(10)-diene-17S-spiro-5'-(2'-oxo-3'-ethyloxazolidine) is performed as described in Example 15 and the oestr-4en-3-one-17S-spiro-5'-(2'-oxo-3'-ethyloxazolidine) obtained is recrystallized from ethyl acetate. M.p. 147° C.; $[\alpha]_D^{20} = -17°$ (c=0.5, chloroform).

EXAMPLE 40

13β-Ethyl-3-methoxygona-2,5(10)-diene-17S-spiro-5'-(2'-oxo-3'-dimethylphosphinoxymethyloxazolidine)

0.85 g. of 13β-ethyl-3-methoxygona-2,5(10)-diene-17S-spiro-5'-(2'-oxooxazolidine) prepared as described in Example 22 are dissolved in 50 ml. of dry tetrahydrofurane. 0.18 g. of sodium hydride containing 20% of paraffine are then added to the solution at room temperature, while stirring. After about 0.5 hours the effervescence ceases. Then 0.60 g. of dimethylphosphinoxymethyl chloride are added and the reaction mixture is stirred at room temperature for 24 hours and boiled for further 10 hours. The reaction mixture is allowed to cool to room temperature, a further 0.18-g. portion of sodium hydride containing 20% of paraffin is added followed after 0.5 hours by the addition of 0.60 g. of dimethylphosphinoximethyl chloride. The boiling is continued for a further 5 hours. Excess sodium hydride is decomposed by the addition of ethanol and the mixture is evaporated. The residue is dissolved in water and ethyl acetate, the ethyl acetate phase is washed with water, dried and evaporated. To the oily residue methanol is added and the crystalline product obtained is filtered and recrystallized from ethyl acetate to yield 0.50 g. of 13β-ethyl-3-methoxygona-2,5(10)-diene-17S-spiro-5'-(2'-oxo-3'-dimethylphosphinoxymethyloxazolidine) melting at 110° to 112° C. $[\alpha]_D^{20} = 0°$ (c=0.5, chloroform).

Following this procedure but starting with the 13β-ethyl-gon-4-en-3-one-17S-spiro-5'-(2'-oxooxazolidine) prepared in Example 23, 13β-ethylgon-4-en-3-one-17S-spiro-5'-(2'-oxo-3'-dimethylphosphinoxymethyloxazolidine) is obtained.

EXAMPLE 41

Tablets weighing about 200 mg. each and having the following composition are prepared:

| | |
|---|---|
| 13β-Ethylgon-4-en-3-one-17S-spiro-5'-(2'-oxo-3'-methyloxazolidine) (micronized) | 25 mg. |
| Corn starch | 128 mg. |
| Polyethylene glycol - 6000 | 40 mg. |
| Talc | 6 mg. |
| Magnesium stearate | 1 mg. |
| | 200 mg. |

The tablets are coated with a film or sugar.

What we claim is:

1. Oestr-4-en-3-one-17S-spiro-5'-(2'-oxo-3'-methyloxazolidine).
2. Androst-4,6-dien-3-one-17S-spiro-5'-(2'-oxo-3'-methyloxyzolidine).
3. 3β-hydroxy-5β,19-cycloandrost-6-ene-17S-spiro-5'-(2'-oxo-3'-methyloxazolidine).
4. 3β-fluoroandrost-5-ene-17S-spiro-5'-(2'-oxo-3'-methyloxazolidine).
5. 13β-ethylgon-5(10)-en-3-one-17S-spiro-5'-(2'-oxo-3'-methyloxazolidine).
6. 13β-ethylgon-4-en-3-one-17S-spiro-5'-(2'-oxo-3'-methyloxazolidine).
7. 13β-ethyl-3-methoximinogon-4-ene-17S-spiro-5'-(2'-oxo-3'-methyloxazolidine).
8. 13β-ethylgona-4,9(10),11-trien-3-one-17S-spiro-5'-(2'-oxo-3'-methyloxazolidine).
9. 13β-ethyl-3-methoxygona-2,5(10)-diene-17S-spiro-5'-(2'-oxo-3'-(1''-cis- propenyl-oxazolidine).
10. A compound of formula I

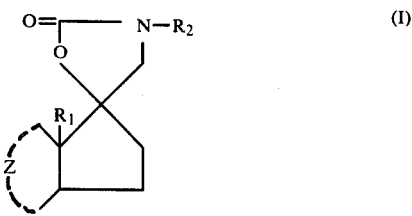

wherein
R₁ is methyl or ethyl, $R_2$ is hydrogen, alkyl having from 1 to 4 carbon atoms, alkenyl having from 1 to 4 carbon atoms or dialkylphosphinoxymethyl having in the alkyl moiety from 1 to 3 carbon atoms each, Z is one of the groups represented by formulae III to XI, XIII and XIV

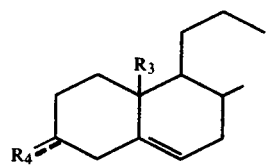
(III)

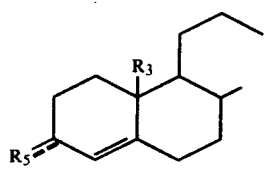
(IV)

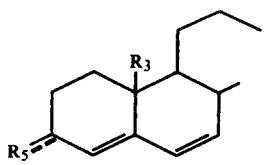
(V)

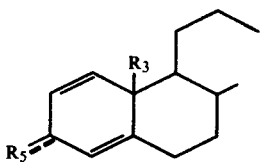
(VI)

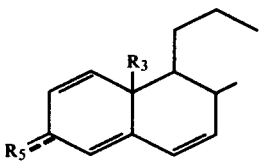
(VII)

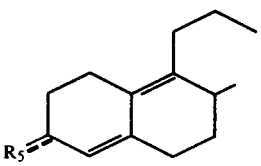
(VIII)

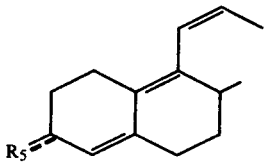
(IX)

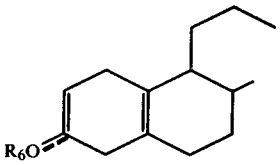
(X)

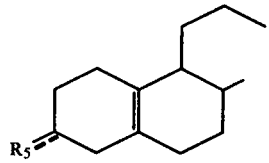
(XI)

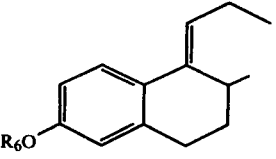
(XIII)

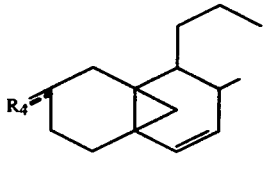

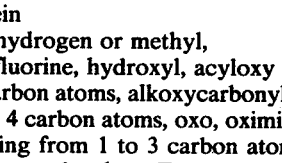
(XIV)

wherein $R_3$ is hydrogen or methyl, $R_4$ is fluorine, hydroxyl, acyloxy having from 1 to 3 carbon atoms, alkoxycarbonyloxy having from 1 to 4 carbon atoms, oxo, oximino or alkoximino having from 1 to 3 carbon atoms in the case of compounds where Z represents Formula III and $R_4$ is hydroxyl, axyloxy having 1 to 3 carbon atoms, alkoxy carbonyl having 1 to 4 carbon atoms, oxo, oximino, or alkoximino having from 1 to 3 carbon atoms where Z represents Formula XIV, $R_5$ is oxo, oximino or alkoximino having from 1 to 3 carbon atoms, and $R_6$ is alkyl having from 1 to 3 carbon atoms, and enantiomers thereof.

* * * * *

UNITED STATES PATENT AND TRADEMARK OFFICE
CERTIFICATE OF CORRECTION

PATENT NO. : 4,180,505
DATED : 25 December 1979
INVENTOR(S) : Sándor Sólyom et al It is certified that error appears in the above-identified patent and that said Letters Patent are hereby corrected as shown below:

Under [19] change "Toldy et al" to -- Sólyom et al --.

Under [75] change "Sándor S. L. Toldy;" to -- Sándor Sólyom; Lajos Toldy; --.

Under [73] change "Vegyeszet" to -- Vegyészeti --.

Signed and Sealed this

First Day of April 1980

[SEAL]

Attest:

SIDNEY A. DIAMOND

Attesting Officer

Commissioner of Patents and Trademarks